(12) United States Patent
Ligouras et al.

(10) Patent No.: US 11,774,517 B2
(45) Date of Patent: Oct. 3, 2023

(54) LEAKAGE AND LOADING DETECTOR CIRCUIT

(71) Applicant: NXP B.V., Eindhoven (NL)

(72) Inventors: Costantino Ligouras, Utrecht (NL); Harry Neuteboom, Eindhoven (NL); Sergio Andrés Rueda Gómez, Eindhoven (NL); Dave Sebastiaan Kroekenstoel, Eindhoven (NL); Peng Zhao, Eindhoven (NL)

(73) Assignee: NXP B. V., Eindhoven (NL)

( * ) Notice: Subject to any disclaimer, the term of this patent is extended or adjusted under 35 U.S.C. 154(b) by 2 days.

(21) Appl. No.: 17/518,258

(22) Filed: Nov. 3, 2021

(65) Prior Publication Data

US 2023/0133063 A1 May 4, 2023

(51) Int. Cl.
*G01R 31/52* (2020.01)
*G01R 31/68* (2020.01)
*A61B 5/145* (2006.01)
*A61B 5/1477* (2006.01)

(52) U.S. Cl.
CPC .............. *G01R 31/52* (2020.01); *G01R 31/68* (2020.01); *A61B 5/1477* (2013.01); *A61B 5/14532* (2013.01)

(58) Field of Classification Search
CPC ................................ G01R 31/52; G01R 31/68
See application file for complete search history.

(56) References Cited

U.S. PATENT DOCUMENTS

| 6,330,697 | B1* | 12/2001 | Clinton | G11C 29/025 |
| | | | | 714/719 |
| 6,426,632 | B1* | 7/2002 | Clunn | G01R 15/183 |
| | | | | 324/424 |
| 7,985,330 | B2 | 7/2011 | Wang et al. | |
| 9,360,447 | B2 | 6/2016 | Shah et al. | |
| 9,443,610 | B1* | 9/2016 | Pan | G11C 29/025 |

(Continued)

*Primary Examiner* — Patrick Assouad
*Assistant Examiner* — Demetrius R Pretlow

(57) ABSTRACT

Various embodiments relate to a detector circuit, including: a voltage source configured to produce a first voltage on a first output, a second voltage on a second output, and third voltage on a third output, wherein the first voltage is greater than the second voltage and the second voltage is greater than the third voltage; a first switch connected to the second output; a sampling capacitor connected to the switch, wherein the sampling capacitor is charged by the voltage source when the switch is closed; a first comparator with one input connected to the first output and a second input connected to the sampling capacitor; a second comparator with one input connected to the third output and a second input connected to the sampling capacitor; a multiplexer with a plurality of inputs configured to be connected to a plurality of terminals of an external circuit and an output connected to the sampling capacitor, the first input of the first comparator, and the first input of the second comparator; and a controller with inputs connected to the first comparator, the second comparator, and a clock generation unit, wherein the controller is configured to produce control signals to control the first switch and the multiplexer and wherein the controller is configured to produce an output signal indicting the presence of a current leak on one of the plurality of terminals.

21 Claims, 5 Drawing Sheets

(56) References Cited

U.S. PATENT DOCUMENTS

| | | | |
|---|---|---|---|
| 11,402,409 B1* | 8/2022 | McNally | G01R 31/2896 |
| 2003/0001585 A1* | 1/2003 | Montrose | G01R 31/2879 |
| | | | 324/519 |
| 2007/0145981 A1 | 6/2007 | Tomita et al. | |
| 2009/0105571 A1 | 4/2009 | Fennell et al. | |
| 2010/0134132 A1* | 6/2010 | Price | G01R 31/31932 |
| | | | 324/756.04 |
| 2012/0218833 A1* | 8/2012 | Yamada | G11C 7/06 |
| | | | 365/226 |
| 2013/0107640 A1* | 5/2013 | Yamada | G11C 8/08 |
| | | | 365/226 |
| 2015/0077314 A1* | 3/2015 | Kim | G09G 3/3233 |
| | | | 345/76 |
| 2016/0351274 A1* | 12/2016 | Pan | G11C 29/50 |
| 2017/0316834 A1* | 11/2017 | Huynh | G11C 16/3422 |
| 2019/0089074 A1* | 3/2019 | Oms | G01R 31/52 |
| 2019/0101585 A1 | 4/2019 | Marques Martins et al. | |
| 2019/0324064 A1* | 10/2019 | Kinsella | G01R 15/183 |
| 2021/0132155 A1* | 5/2021 | Kim | G01R 31/3842 |
| 2022/0393697 A1* | 12/2022 | Adusumalli | H03M 3/458 |

\* cited by examiner

LEAKAGE AND LOADING DETECTOR CIRCUIT

TECHNICAL FIELD

Various exemplary embodiments disclosed herein relate generally to a circuit that monitors its external terminals to detect current leakage when nothing is connected to the circuit or the presence of a load between terminals of the circuit.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a detector circuit, including: a voltage source configured to produce a first voltage on a first output, a second voltage on a second output, and third voltage on a third output, wherein the first voltage is greater than the second voltage and the second voltage is greater than the third voltage; a first switch connected to the second output; a sampling capacitor connected to the switch, wherein the sampling capacitor is charged by the voltage source when the switch is closed; a first comparator with one input connected to the first output and a second input connected to the sampling capacitor; a second comparator with one input connected to the third output and a second input connected to the sampling capacitor; a multiplexer with a plurality of inputs configured to be connected to a plurality of terminals of an external circuit and an output connected to the sampling capacitor, the first input of the first comparator, and the first input of the second comparator; and a controller with inputs connected to the first comparator, the second comparator, and a clock generation unit, wherein the controller is configured to produce control signals to control the first switch and the multiplexer and wherein the controller is configured to produce an output signal indicting the presence of a current leak on one of the plurality of terminals.

Further various embodiments relate to a sensor system, including: a sensor; and a sensor interface circuit including a detector circuit including: a voltage source configured to produce a first voltage on a first output, a second voltage on a second output, and third voltage on a third output, wherein the first voltage is greater than the second voltage and the second voltage is greater than the third voltage; a first switch connected to the second output; a sampling capacitor connected to the switch, wherein the sampling capacitor is charged by the voltage source when the switch is closed; a first comparator with one input connected to the first output and a second input connected to the sampling capacitor; a second comparator with one input connected to the third output and a second input connected to the sampling capacitor; a multiplexer with a plurality of inputs configured to be connected to a plurality of terminals of an external circuit and an output connected to the sampling capacitor, the first input of the first comparator, and the first input of the second comparator; and a controller with inputs connected to the first comparator, the second comparator, and a clock generation unit, wherein the controller is configured to produce control signals to control the first switch and the multiplexer and wherein the controller is configured to produce an output signal indicting the presence of a current leak on one of the plurality of terminals.

Various embodiments are described, wherein the voltage source includes a bandgap voltage source and a bandgap buffer.

Various embodiments are described, further including a plurality of additional switches connected between each of the plurality of terminals and ground, wherein the control signals produced by the controller include signals to control the plurality of additional switches.

Various embodiments are described, wherein the controller is configured to: close the first switch to charge the sampling capacitor; connect one of the plurality terminals to the sampling capacitor using the multiplexer; open the first switch; and monitor the outputs of the first comparator and the second comparator to determine if there is a current leak on the connected terminal.

Various embodiments are described, wherein the controller is further configured to measure the leakage current.

Various embodiments are described, wherein the output signal further indicates a connection to the external circuit.

Various embodiments are described, wherein the controller is configured to: connect all but one of the plurality of terminals to ground using the plurality of additional switches; close the first switch to charge the sampling capacitor; open the first switch; connect one terminal not connected to ground to the sampling capacitor using the multiplexer; and monitor the outputs of the first comparator and the second comparator to determine if the detection circuit is connected to the external circuit.

Various embodiments are described, wherein the controller is further configured to measure a resistance of the external circuit.

Various embodiments are described, wherein the output signal indicates a connection to the external circuit when a voltage on the sampling capacitor drops below the third voltage.

Various embodiments are described, wherein the output signal indicates the presence of a current leak when a voltage on the sampling capacitor drops below the third voltage.

Further various embodiments relate to a method for detecting a current leak in an external circuit using a detector circuit, including: producing a first voltage on a first output of a voltage source, a second voltage on a second output of a voltage source, and third voltage on a third output of a voltage source, wherein the first voltage is greater than the second voltage and the second voltage is greater than the third voltage; charging a sampling capacitor using the second voltage by closing a switch connected between the sampling capacitor and the voltage source; opening the first switch; comparing a voltage on the sampling capacitor with the first output; comparing a voltage on the sampling capacitor with the second output; selecting one of a plurality of inputs configured to be connected to a plurality of terminals of an external circuit; connecting the selected input to the sampling capacitor; producing control signals, by a controller, to control the first switch and the selecting one of a plurality of inputs; and producing an output signal indicting the presence of a current leak on one of the plurality of terminals.

Various embodiments are described, producing, by the controller, signals to control a plurality of additional switches connected between each of the plurality of terminals and ground.

Various embodiments are described, further including measuring, by the controller, the leakage current.

Various embodiments are described, wherein the output signal further indicates a connection to the external circuit.

Various embodiments are described, further including; connecting all but one of the plurality of terminals to ground using the plurality of additional switches; closing the first switch to charge the sampling capacitor; opening the first switch; connecting one terminal not connected to ground to the sampling capacitor using the multiplexer; and monitoring the outputs of the first comparator and the second comparator to determine if the detection circuit is connected to the external circuit.

Various embodiments are described, further including measuring, by the controller, a resistance of the external circuit.

Various embodiments are described, wherein the output signal indicates a connection to the external circuit when a voltage on the sampling capacitor drops below the third voltage.

Various embodiments are described, wherein the output signal indicates the presence of a current leak when a voltage on the sampling capacitor drops below the third voltage.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
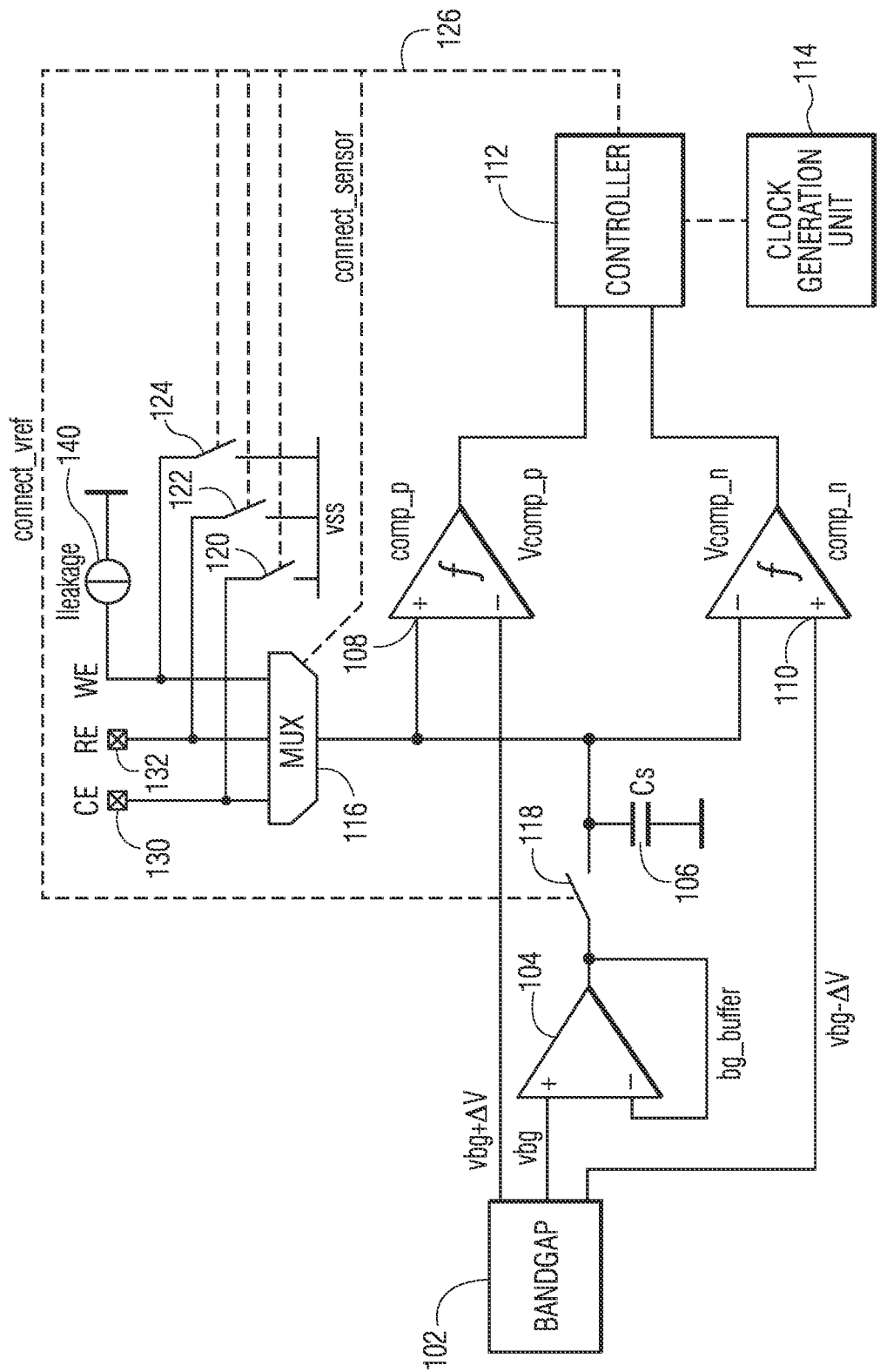
FIG. 1 illustrates a diagram of a detection circuit that may be used to detect current leakage in and connectivity to a circuit.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

During the production of circuits including circuits to interface electrochemical sensors, a monitoring circuit may be used to measure a pad/node leakage during production testing. Further, once the electrochemical sensor is placed in use, the monitoring circuit may verify that the electrochemical sensor has been successfully connected and is operating. One example of such an electrochemical sensor is a continuous glucose monitoring sensor. A continuous glucose monitoring (CGM) sensor is hydrated and then variations in the glucose level may be measured through terminals of the chip interfacing the CGM sensor so that the glucose level may be monitored. The CGM sensor may include three terminals: CE; RE, and WE. Likewise, the circuit interfacing the CGM sensor may also have CE, RE, and WE terminals. The RE terminal is a reference electrode of the sensor that maintains a constant reference voltage for WE electrode. The WE terminal is a work electrode of the sensor where the electrochemical reaction occurs, hence the current is generated and read. The CE terminal is a counter electrode of the sensor that is a connection to the electrolyte for current to compensate for reaction at the WE terminal. The current reading of a CGM circuit needs to be accurate to a few pA, and potential leakage on the RE pin can damage the sensor. During production, each of these terminals may be tested to determine if the terminal has any current leakage in order to prevent damage to the CGM sensor via leakage at the RE terminal. Due to the low-power nature of wearables electronics applications where a CGM or another sensor is deployed, it is equally important to be able to detect when a CGM sensor is physically connected to an integrated circuit and hydrated by the interstitial fluid on the human body, i.e., when the dedicated CGM sensor analog front-end (AFE) may start operating. Further, once the CGM circuit is in use, a resistance should appear between the RE and WE terminals of the CGM circuit. A detector circuit is described herein that may be used to detect current leakage of the various terminals of a circuit. Further, the detector circuit may be able to monitor the sensor during use to verify that it is properly connected and loaded, i.e., hydrated in the case of a CGM sensor. The detector circuit described herein will avoid the use of expensive and complex analog to digital circuits and other such circuits to result in a detector circuit that is accurate and inexpensive to implement.

A glucose monitoring circuit with three terminals is used as an example herein, but other types of circuits or sensors that requires leakage detection during production and/or determining the connection and operation of the circuit during use. Further, the detection circuit described herein may be used with circuits that have any number of terminals that need to be monitored.

FIG. 1 illustrates a diagram of a detection circuit that may be used to detect current leakage and connectivity between pins in a circuit. The monitored system is a CGM system where the leakage of a CGM readout circuit and the hydration of the CGM sensor are detected. The detection circuit 100 includes a bandgap voltage reference 102, bandgap buffer 104, sampling capacitor $C_s$ 106, first comparator 108, second comparator 110, controller 112, clock generation unit 114, and a mux 116. The bandgap voltage reference 102 produces three output voltages: $V_{bg}$ and $V_{bg}+/-\Delta V$. The voltage $V_{bg}$ is buffered by the bandgap buffer 104 to isolate the bandgap voltage from the sampling capacitor $C_s$ 106 as the sensor capacitance can be much larger than the integrated $C_s$, and in that case the bandgap voltage may jump down when connected to the empty parasitic capacitor. In this example, the bandgap buffer 104 is implemented with an operational amplifier, but other implementations may be used as well. The switch 118 is connected between the bandgap buffer 104 and the sampling capacitor $C_s$ 106. When the switch 118 is closed the buffered bandgap voltage $V_{bg}$ is sampled by charging the sampling capacitor $C_s$ 106. The switch 118 may be controlled by a control signal 126 output by the controller 112. The switch 118 may be implemented using any type of switch typically used in electrical circuits.

The first comparator 108 receives $V_{bg}+\Delta V$ as one input and the sampling capacitor voltage $V_{cap}$ as the other input. The output of the first comparator 108 indicates whether the sampling capacitor voltage $V_{cap}$ is above or below $V_{bg}+\Delta V$. The second comparator 110 receives $V_{bg}-\Delta V$ as one input and the sampling capacitor voltage $V_{cap}$ as the other input. The output of the second comparator 110 indicates whether the sampling capacitor voltage $V_{cap}$ is above or below $V_{bg}-\Delta V$. The comparators 108, 110 may be implemented using operational amplifiers or any other typically used circuit.

The controller 112 receives the outputs of the first comparator 108 and the second comparator 112 and a clock signal from the clock generation unit 114. The controller 112 produces various control signals 126 that are used to control the MUX 116 and the various switches 118, 120, 122, 124. The operation of the controller 112 will be further described below. The controller 112 may be implemented using a small programmable microcontroller, a processor, a state machine, or dedicated logic that implements the desired control features and steps.

The MUX 116 is connected to the three terminals CE 130, RE 132, and WE 134 of a chip interfacing the CGM sensor. The output of the MUX 116 is connected to a node between the sampling capacitor $C_s$ 106 and the first comparator 108 and the second comparator 110. The MUX 116 receives a control signal 126 from the controller 112 that controls which of the three inputs (i.e., CE 130, RE 132, and WE 134) if any are connected to the output of the MUX 116. The MUX 116 is shown as having three inputs, but the MUX 116 may have fewer or more inputs depending upon the number of inputs that the circuit to be monitored has.

The switches 120, 122, 124 are connected to the terminals 130, 132, 134. The switches 120, 122, 124 are also connected to ground which is designated as VSS, so that when any of the switches 120, 122, 124 are closed, the corresponding terminal is connected to ground. Three switches are illustrated, but fewer or more switches may be used depending upon the number of circuit inputs that need to be monitored.

The detection circuit 100 has two modes of operation including a leakage current detection mode and a sensor connection and/or hydration mode. The leakage current detection mode may be used during production to detect if any of the terminals of the chip exhibit excessive current leakage. The sensor connection and/or hydration mode may be used to detect that the sensor is properly connected and/or properly hydrated (as in the case of a CGM sensor).

Figure 2:
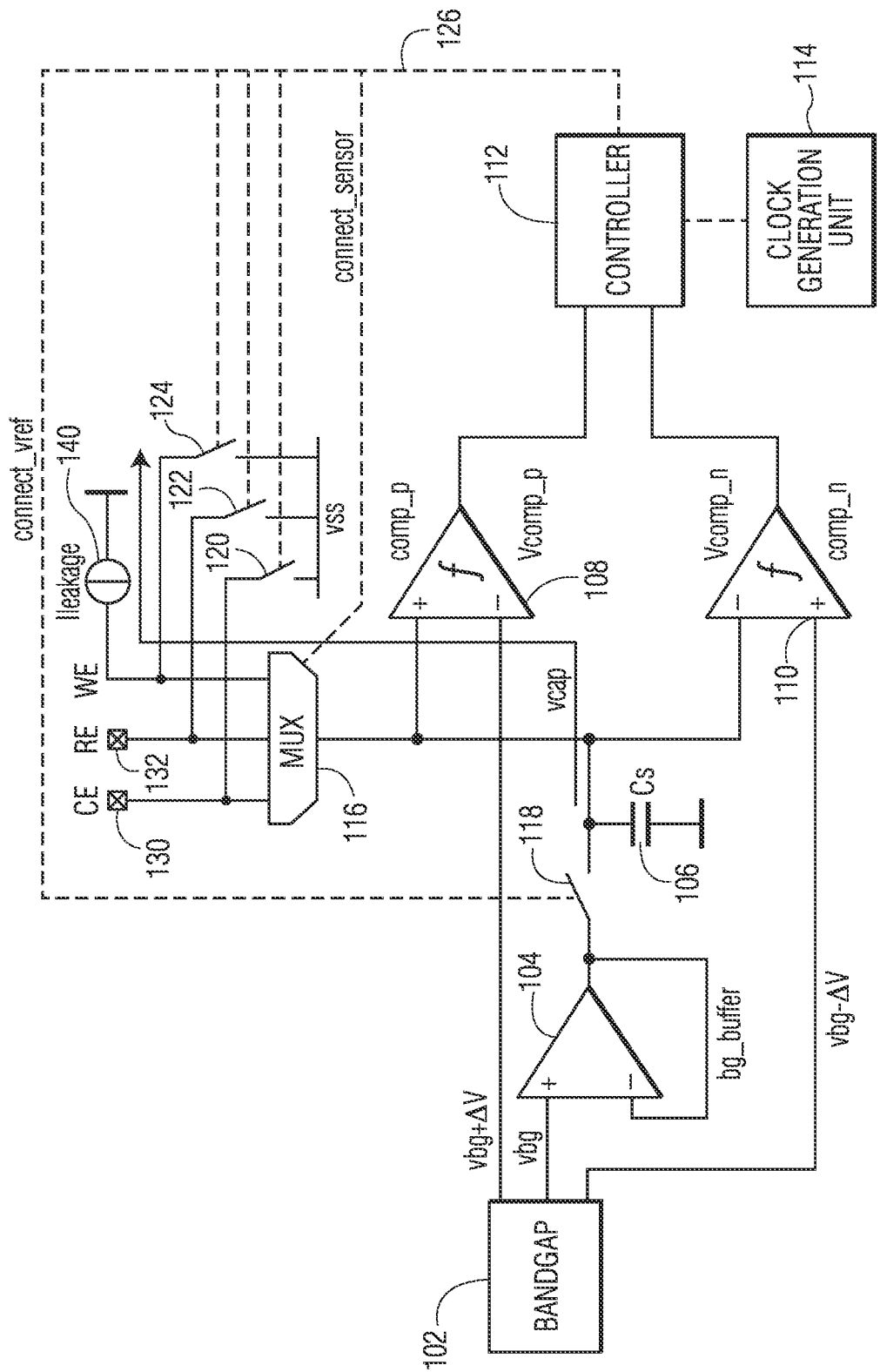
FIG. 2 illustrates the operation circuit during the leakage current detection mode.
Figure 3:
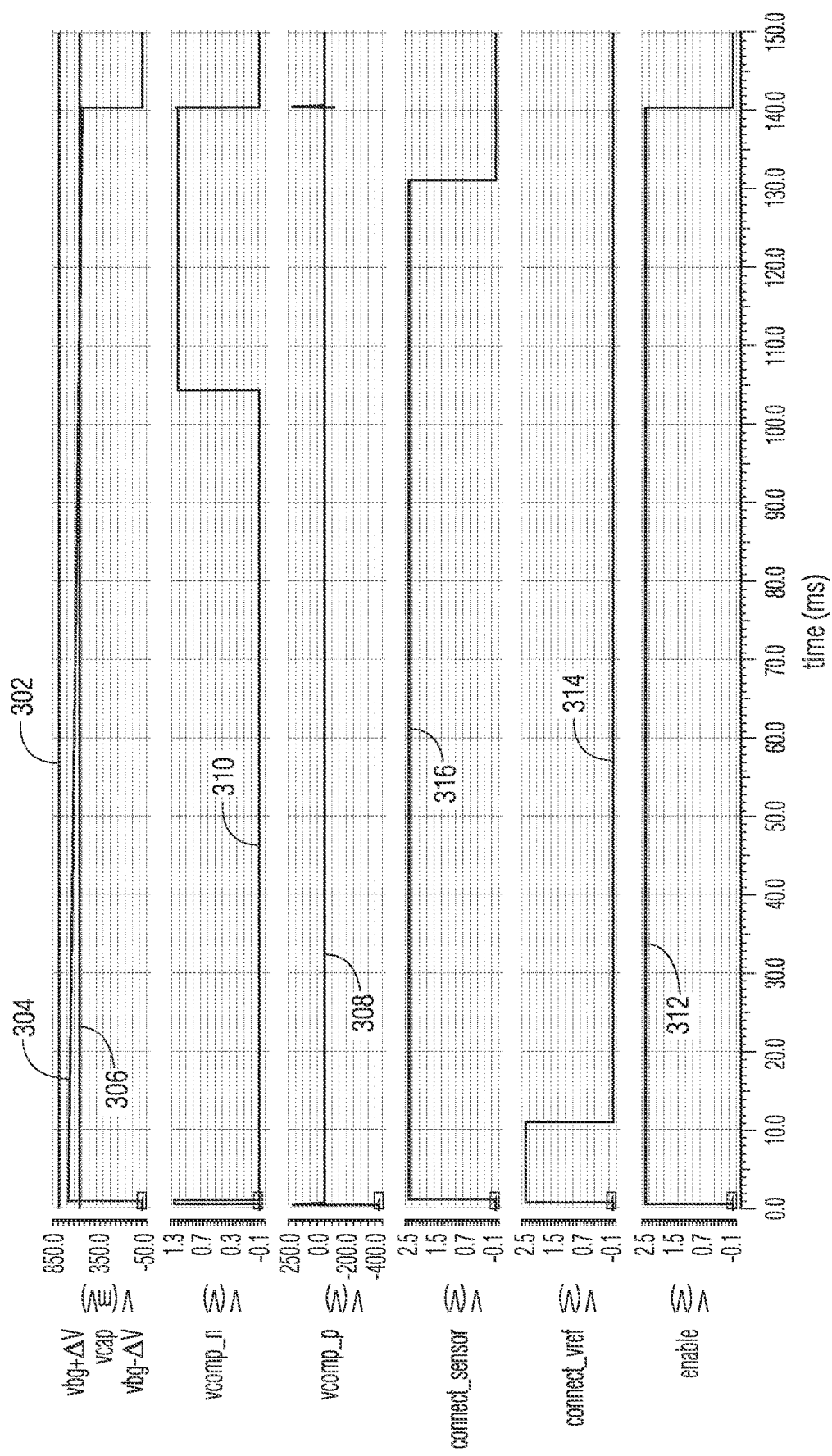
FIG. 3 illustrates plots of various voltages and control signals during the leakage current detection mode.

FIG. 2 illustrates the operation of the detection circuit during the leakage current detection mode. FIG. 3 illustrates plots of various voltages and control signals in the detection circuit during the leakage current detection mode. The leakage current detection mode includes the following steps: open the switches 120, 122, 124 connecting the terminals CE 130, RE 132, and WE 134 to ground; sample the bandgap voltage on sampling capacitor $C_s$ 106 by closing switch 118; connect the terminal to be measured to $C_s$ by using the MUX 116; and open the switch 118 and then the controller 112 monitors the comparator outputs for a period of time. This process may be repeated for each of the terminals as needed.

FIG. 2 illustrates a current leakage source 140 connected to the WE terminal 134. As this leakage source is now connected to the sampling capacitor $C_S$, the leakage source will cause the sense capacitor voltage $V_{cap}$ to decrease or increase over time. As a result, the output of the first comparator 108 will indicate that the sense capacitor voltage $C_{cap}$ is now greater than $V_{bg}+\Delta V$ or the output of the second comparator 110 will indicate that the sense capacitor voltage $C_{cap}$ is now less than $V_{bg}-\Delta V$ after a certain time interval based upon the clock signal from the clock generation unit. A counter in the controller 112 may count clock cycles from the clock generation unit 114, and the leakage current may be derived by measuring the time between the opening of the switch 118 and the time when the sense capacitor voltage $C_{cap}$ falls below $V_{bg}-\Delta V$ or above $V_{bg}+\Delta V$ as follows:

$$\pm I_{leak} = \pm \frac{\Delta V * C_s}{\Delta t}$$

If measuring the actual value of the leakage current is not essential, and the measurement objective is to only detect a maximum allowed leakage current in production, the programmable parameter $\Delta t$ may be fixed by the controller. Note that this circuit can detect both leakage current polarities on a node, i.e., a current flowing into the sense capacitor $C_s$ 106 or a current flowing out of the sense capacitor $C_s$ 106.

FIG. 3 includes plots of the voltages $V_{bg}+\Delta V$ 302, $V_{cap}$ 304, and $V_{bg}-\Delta V$ 306. Further, plots of the output for the first comparator 308 and the second comparator 310 are illustrated. A plot of an enable signal 312 that is used to enable the operation of the detection circuit is also illustrated. A plot of a control signal connect_vref 314 illustrates the time when the switch 118 is closed to charge the sampling capacitor $C_s$ 106. Finally, a control signal connect_sensor 316 illustrates the time when the MUX 116 connects one of the terminals 130, 132, 134 to the sampling capacitor $C_s$ 106. When the enable signal 312 goes high the detection circuit can begin to operate. At this point $V_{cap}$ is 0V so the output of the second comparator 110 goes high because $V_{cap}$ is below $V_{bg}-\Delta V$. The output 308 of the first comparator remains zero because $V_{cap}$ is below $V_{bg}+\Delta V$ except for startup artifacts which will be digitally gated out. Shortly after the enable signal 312 goes high, the signal connect_ref 314 goes high to close the switch 118 for a period of time so that the sampling capacitor $C_s$ 106 is charged. Also the connect_sensor signal 316 goes high to enable the MUX 116 to connect one of the terminals to be tested to the sampling capacitor $C_s$ 106. As a result, the plot of $V_{cap}$ 304 increases to the value of $V_{bg}$ that causes the output 310 of the second comparator to become low because $V_{cap}$ is now above $V_{bg}-\Delta V$. Over time the value of Vcap decreases because of a current leak, and once $V_{cap}$ 304 decreases below $V_{bg}-\Delta V$ 306, the output 310 of the second comparator goes high. This indicates to the controller 112 that there is a current leak and the controller may indicate to a user or testing apparatus that the pin being tested has a current leak. Then the enable signal 312 goes low, which disables the detection circuit so the output 310 of the second comparator goes low. Further, one of the switches 120, 122, 124 corresponding to the terminal being tested may be closed to ground the sampling capacitor $C_s$ 106 to discharge it so that its output 304 goes to 0V. In other embodiments this may not be done in order to save power.

Figure 4:
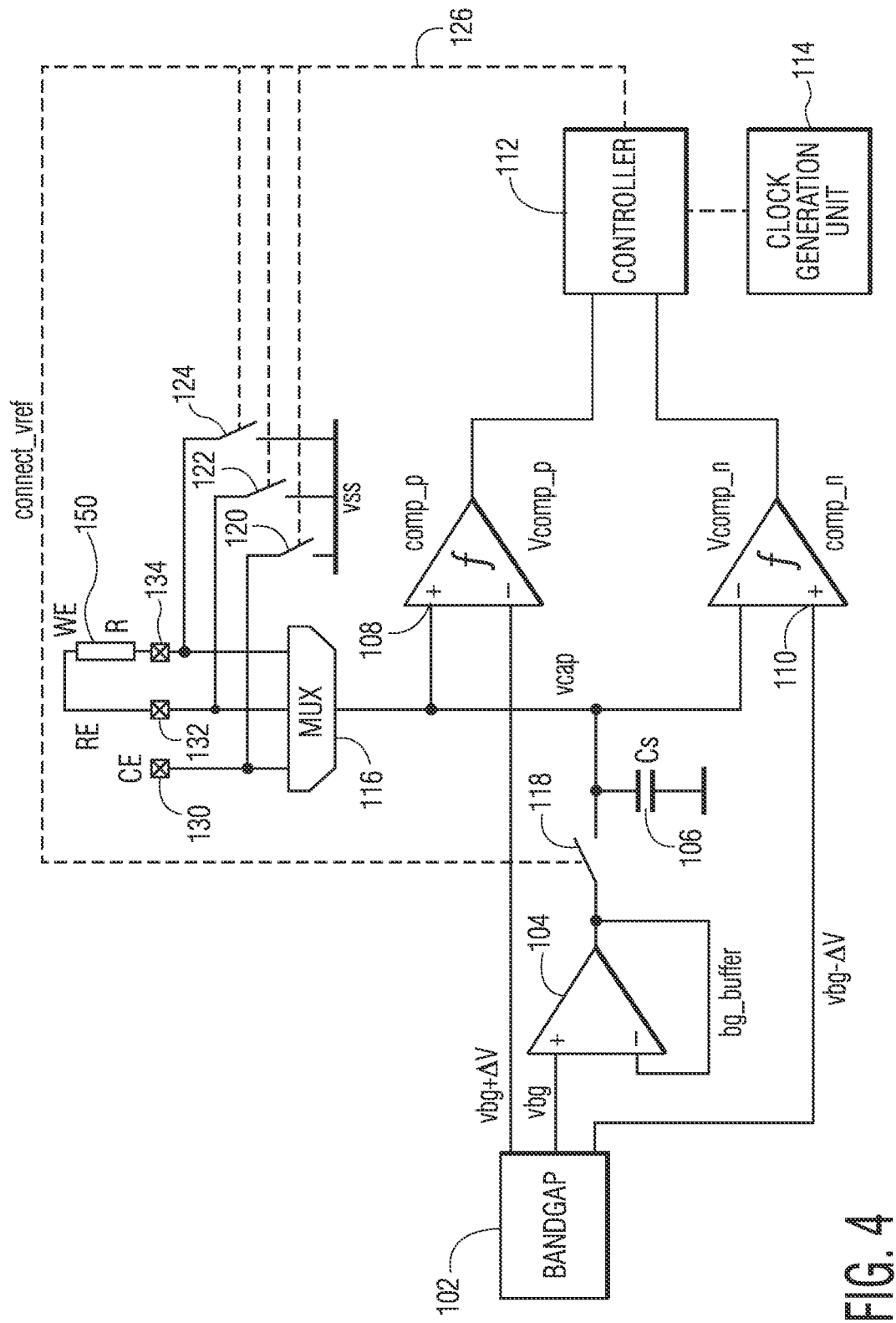
FIG. 4 illustrates the operation of the circuit during the sensor connection and/or hydration mode.
Figure 5:
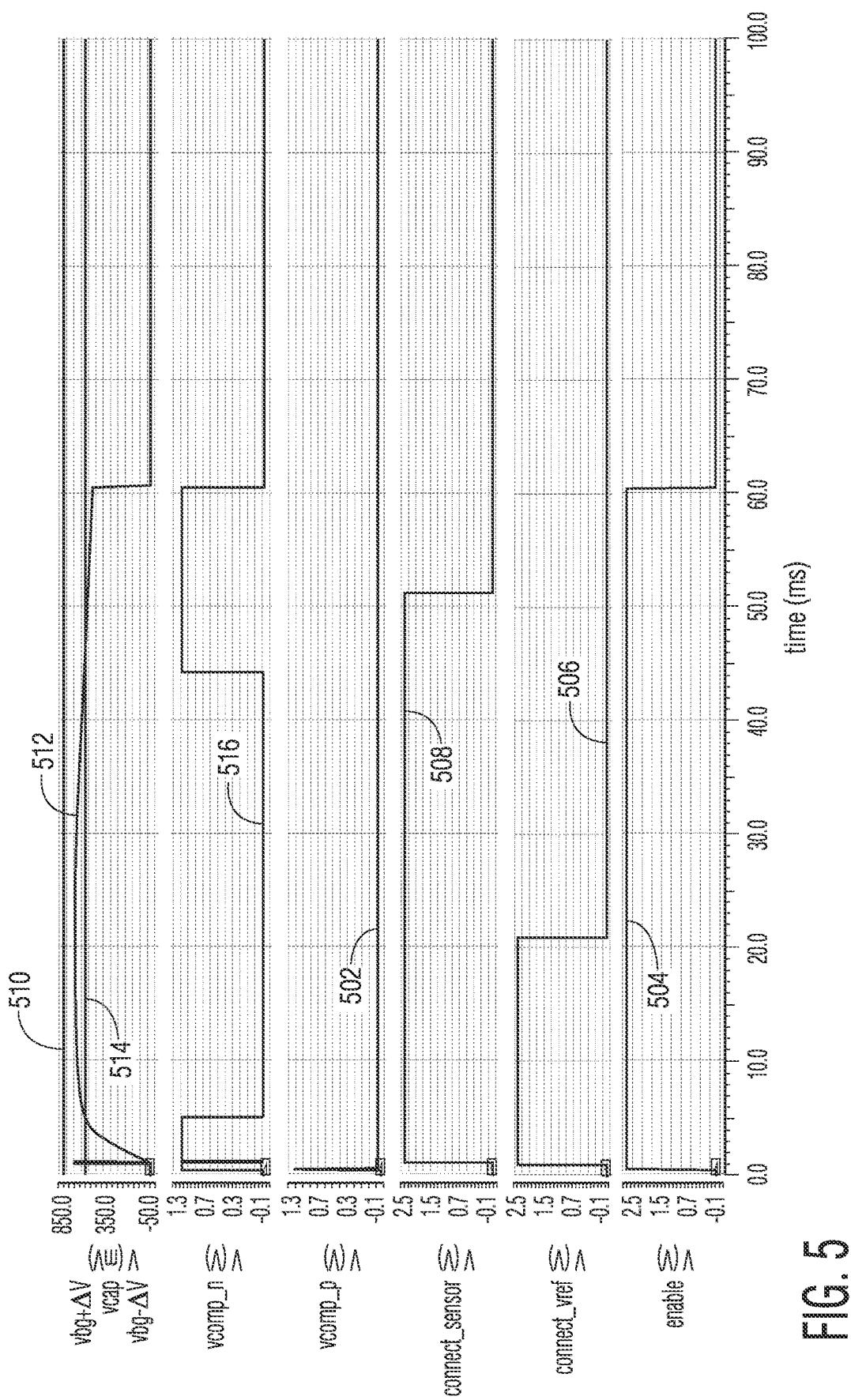
FIG. 5 illustrates plots of various voltages and control signals during the sensor connection and/or hydration mode.

FIG. 4 illustrates the operation of the detection circuit during the sensor connection and/or hydration mode. FIG. 5 illustrates plots of various voltages and control signals in the detection circuit during the sensor connection and/or hydration mode. The sensor connection and/or hydration mode includes the following steps: connect the CE terminal 130 and the WE terminal 134 to ground; sample the bandgap voltage on sampling capacitor $C_s$ 106 by closing switch 118; connect the RE terminal 132 to the sampling capacitor $C_s$ 106 using the MUX 116 and then open the switch 118; and monitor the comparator outputs using the controller 112 for a period of time to determine if $V_{cap}$ decays indicating connection and/or hydration and to determine a load resistance value R if desired.

A hydrated CGM sensor connected between WE and RE will create an impedance to ground in parallel to the discharging sampling capacitor $C_s$ 106. A maximum impedance can be measured by defining a programmable time interval after opening the switch 118 and the voltage difference $\Delta V$ on the output of the second comparator 110.

The discharging voltage on the sampling capacitor $C_s$ 106 will have the following exponential equation:

$$V_{cap} = V_{bg}\left(e^{-\frac{t}{RC_s}}\right).$$

Accordingly, knowing the value of $V_{cap}$ at a specific time t, will allow the value of R to be calculated. This value then can be used to determine if the sensor is connected and is properly operating/hydrated.

FIG. 5 includes plots of voltages at voltages $V_{bg}+\Delta V$ 510, $V_{cap}$ 512, and $V_{bg}-\Delta V$ 514. A plot of a control signal enable_and_ground_CE_WE 504 is shown that indicates when the terminals CE 130 and WE 134 are grounded, and the detection circuit is enabled. A plot of a control signal connect_vref 506 illustrates the time when the switch 118 is closed to charge the sampling capacitor $C_s$ 106. A control signal connect_sensor 508 illustrates the time when the MUX 116 connects the RE terminal 132 to the sampling capacitor $C_s$ 106. Finally, a plot of the output 502 of the first comparator 108 and the output 516 of the second comparator 110 are illustrated.

When the enable signal 504 goes high, the terminals CE 130 and WE 134 are grounded. This causes the voltage at the CE terminal 130 and WE terminal 134 to be grounded and go to 0V. Further, at this point the output 516 of the second comparator 110 will go high indicating that $V_{cap}$ 512 is below $V_{bg}-\Delta V$ 514. Next, the signal connect_vref 506 goes high to close the switch 118 for a period of time so that the sampling capacitor $C_s$ 106 is charged. This results in $V_{cap}$ 514 increasing to the voltage level of $V_{bg}$, and the output of the second comparator 110 will go low indicating that $V_{cap}$ 512 is above $V_{bg}-\Delta V$ 514. Shortly thereafter the connect_sensor signal 508 goes high to enable the MUX 116 to connect the RE terminal 132 to the sampling capacitor $C_s$ 106. Over time the value of $V_{cap}$ decreases because the charge on the sampling capacitor 106 is dissipated in the resistance R (as described by the equation above), and once $V_{cap}$ 512 decreases below $V_{bg}-\Delta V$ 514, the output 516 of the second comparator goes high. This indicates to the controller 112 that the sensor is connected and/or hydrated. Based upon the voltage change and the amount of time taken to result in the voltage change, a value for R may be calculated as described above. The enable signal 504 can then go low to disable the operation of the detection circuit.

In an alternative embodiment, for a better resolution, it is also possible to calibrate the detection circuit in the leakage monitor mode by applying an external known current and repeating the leakage measurement. The application of the known current allows for the calculation of a calibration constant that is used to compensate the repeated leakage measurement.

The values of $V_{bg}$ and $\Delta V$ may be programmable and allow for the ability to detect a wide range of leakage currents and resistance values.

The detection circuit described herein may effectively measure the leakage of a node/pad during chip or integrated circuit (IC) test production to help identified faulty samples to be discarded or to detect a finite impedance between two electrodes in order to wake-up more power consuming sensor readout circuitry during application. The detection circuit does not require any ADC or complex circuitry. Further the detection circuit can be easily calibrated, and it can be programmed for a wide range of leakage currents and resistance values.

It should be appreciated by those skilled in the art that any block diagrams herein represent conceptual views of illustrative circuitry embodying the principles of the invention.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in anyway limit the invention, which is defined only by the claims.

What is claimed is:

1. A detector circuit configured to be coupled to a voltage source configured to produce a first voltage on a first output, a second voltage on a second output, and third voltage on a third output, wherein the first voltage is greater than the second voltage and the second voltage is greater than the third voltage; the detector circuit comprising:
   a first switch configured to be connected to the second output;
   a sampling capacitor connected to the first switch, wherein the sampling capacitor is configured to be charged by the voltage source when the switch is closed;
   a first comparator with a first input configured to be connected to the first output and a second input connected to the sampling capacitor;
   a second comparator with a first input configured to be connected to the third output and a second input connected to the sampling capacitor;
   a multiplexer with a plurality of inputs configured to be connected to a plurality of terminals of an external circuit and an output connected to the sampling capacitor, the first second input of the first comparator, and the first second input of the second comparator; and
   a controller with inputs connected to the first comparator, and the second comparator,
   wherein the controller is configured to produce control signals to control the first switch and the multiplexer and
   wherein the controller is configured to produce an output signal indicating the presence of a current leak on at least one of the plurality of terminals.

2. The detection circuit of claim 1, wherein the voltage source includes a bandgap voltage source and a bandgap buffer.

3. The detection circuit of claim 1, further comprising a plurality of additional switches connected between each of the plurality of terminals and ground, wherein the control signals produced by the controller include signals to control the plurality of additional switches.

4. The detection circuit of claim 1, wherein the controller is configured to:
    close the first switch to charge the sampling capacitor;
    connect one of the plurality terminals to the sampling capacitor using the multiplexer;
    open the first switch; and
    monitor the outputs of the first comparator and the second comparator to determine if there is a current leak on the connected terminal.

5. The detection circuit of claim 4, wherein the controller is further configured to measure the leakage current.

6. The detection circuit of claim 3, wherein the output signal further indicates a connection to the external circuit.

7. The detection circuit of claim 6, wherein the controller is configured to:
    connect all but one of the plurality of terminals to ground using the plurality of additional switches;
    close the first switch to charge the sampling capacitor;
    open the first switch;
    connect one terminal not connected to ground to the sampling capacitor using the multiplexer; and
    monitor the outputs of the first comparator and the second comparator to determine if the detection circuit is connected to the external circuit.

8. The detection circuit of claim 7, wherein the controller is further configured to measure a resistance of the external circuit.

9. The detection circuit of claim 6, wherein the output signal indicates a connection to the external circuit when a voltage on the sampling capacitor drops below the third voltage.

10. The detection circuit of claim 1, wherein the output signal indicates the presence of a current leak when a voltage on the sampling capacitor drops below the third voltage.

11. A sensor system, comprising:
    a sensor; and
    a sensor interface circuit including a detector circuit comprising:
    a voltage source configured to produce a first voltage on a first output, a second voltage on a second output, and third voltage on a third output, wherein the first voltage is greater than the second voltage and the second voltage is greater than the third voltage;
    a first switch connected to the second output;
    a sampling capacitor connected to the switch, wherein the sampling capacitor is charged by the voltage source when the switch is closed;
    a first comparator with one input connected to the first output and a second input connected to the sampling capacitor;
    a second comparator with one input connected to the third output and a second input connected to the sampling capacitor;
    a multiplexer with a plurality of inputs configured to be connected to a plurality of terminals of an external circuit and an output connected to the sampling capacitor, the first input of the first comparator, and the first input of the second comparator; and
    a controller with inputs connected to the first comparator, the second comparator, and a clock generation unit, wherein the controller is configured to produce control signals to control the first switch and the multiplexer and wherein the controller is configured to produce an output signal indicating the presence of a current leak on one of the plurality of terminals.

12. The sensor system of claim 11, wherein the voltage source includes a bandgap voltage source and a bandgap buffer.

13. The sensor system of claim 1, wherein the detection circuit further comprises a plurality of additional switches connected between each of the plurality of terminals and ground, wherein the control signals produced by the controller include signals to control the plurality of additional switches.

14. The sensor system of claim 1, wherein the controller is configured to:
    close the first switch to charge the sampling capacitor;
    connect one of the plurality terminals to the sampling capacitor using the multiplexer;
    open the first switch; and
    monitor the outputs of the first comparator and the second comparator to determine if there is a current leak on the connected terminal.

15. The sensor system of claim 14, wherein the controller is further configured to measure the leakage current.

16. The sensor system of claim 13, wherein the output signal further indicates a connection to the sensor.

17. The sensor system of claim 16, wherein the controller is configured to:
    connect all but one of the plurality of terminals to ground using the plurality of additional switches;
    close the first switch to charge the sampling capacitor;
    open the first switch;
    connect one terminal not connected to ground to the sampling capacitor using the multiplexer; and
    monitor the outputs of the first comparator and the second comparator to determine if the interface circuit is connected to the sensor.

18. The sensor system of claim 17, wherein the controller is further configured to measure a resistance of the sensor.

19. The sensor system of claim 16, wherein the output signal indicates a connection to the sensor when a voltage on the sampling capacitor drops below the third voltage.

20. The sensor system of claim 11, wherein sensor is one of a electrochemical sensor and a continuous glucose monitoring sensor.

21. A detector circuit configured to be coupled to a voltage source producing a first voltage greater than a second voltage and a third voltage less than the second voltage, the detector circuit comprising:
    a switch configured to receive the second voltage;
    a sampling capacitor having a first end coupled to the switch, wherein the sampling capacitor is configured to be charged by the second voltage when the switch is closed;
    a first comparator having a first input configured to receive the first voltage, a second input coupled to a second end of the sampling capacitor, and an output;
    a second comparator having a first input configured to receive the third voltage, a second input connected to the second end of the sampling capacitor, and an output;
    wherein the second end of the sampling capacitor, the second input of the first comparator, and the second input of the second comparator are configured to be coupled to an external circuit;
    a controller coupled to the switch, the output from the first comparator, and the output from the second comparator; and wherein the controller is configured to produce an output signal indicating a presence of a current leak in the external circuit if the output of either the first comparator or the second comparator generates a signal after the switch is opened.

* * * * *